United States Patent
Mertens et al.

(10) Patent No.: US 6,174,327 B1
(45) Date of Patent: *Jan. 16, 2001

(54) STENT DEPLOYMENT APPARATUS AND METHOD

(75) Inventors: Steven P. Mertens, Plymouth; Tracee E. J. Eidenschink, Wayzata; Timothy J. Mickley, Elk River, all of MN (US)

(73) Assignee: Scimed Life Systems, Inc., Maple Grove, MN (US)

(*) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 09/032,620

(22) Filed: Feb. 27, 1998

(51) Int. Cl.$^7$ ........................................ A61F 2/06
(52) U.S. Cl. ........................................ 623/1.11; 606/108
(58) Field of Search ................. 606/108, 194; 623/1.11

(56) References Cited

U.S. PATENT DOCUMENTS

| | | | |
|---|---|---|---|
| 4,950,227 | 8/1990 | Savin et al. | 604/8 |
| 5,053,008 | 10/1991 | Bajaj | 601/104 |
| 5,226,889 | 7/1993 | Sheiban | 601/101 |
| 5,320,605 | 6/1994 | Sahota | 601/101 |
| 5,409,495 | 4/1995 | Osborn | 606/108 |
| 5,425,709 | 6/1995 | Gambale | 604/96 |
| 5,456,694 | 10/1995 | Marin et al. | 606/198 |
| 5,514,093 | 5/1996 | Ellis et al. | 604/103 |
| 5,522,883 | 6/1996 | Slater et al. | 623/1 |
| 5,534,007 | 7/1996 | St. Germain et al. | 606/108 |
| 5,545,209 | * 8/1996 | Roberts et al. | 606/108 |
| 5,571,086 | 11/1996 | Kaplan et al. | 604/96 |
| 5,613,949 | 3/1997 | Miraki | 601/101 |
| 5,628,755 | 5/1997 | Heller et al. | 606/108 |
| 5,632,760 | 5/1997 | Sheiban et al. | 606/191 |
| 5,634,901 | 6/1997 | Alba et al. | 604/96 |
| 5,634,928 | 6/1997 | Fischell et al. | 606/108 |
| 5,639,274 | * 6/1997 | Fischell et al. | 606/108 |
| 5,676,654 | 10/1997 | Ellis et al. | 604/103 |
| 5,693,066 | 12/1997 | Rupp et al. | 606/198 |
| 5,697,948 | 12/1997 | Marin et al. | 606/198 |
| 5,725,535 | 3/1998 | Hedge et al. | 606/108 |
| 5,733,299 | 3/1998 | Sheiban et al. | 606/192 |
| 5,743,874 | 4/1998 | Fischell et al. | 604/98 |
| 5,807,398 | * 9/1998 | Shaknovich | 606/108 |
| 5,951,569 | * 9/1999 | Tuckey et al. | 606/108 |
| 5,961,536 | * 10/1999 | Mickley et al. | 606/108 |

FOREIGN PATENT DOCUMENTS

WO 96/36298   11/1996   (WO).

* cited by examiner

Primary Examiner—Michael H. Thaler
(74) Attorney, Agent, or Firm—Westman, Champlin, & Kelly, P.A.

(57) ABSTRACT

An improved deployment system deploys a stent to maintain the patency of a dilated vessel. The improved stent deployment system is adapted for deployment with a balloon catheter. The stent deployment system includes an expandable stent sheath for supporting the stent for deployment. The stent sheath is movably coupled to a catheter shaft and is relatively short in comparison to the catheter shaft. The stent sheath is movably coupled to the catheter shaft for movement between a retracted position and an advanced deployment position aligned with the balloon for expansion via the balloon for deployment of the stent supported thereby.

21 Claims, 12 Drawing Sheets

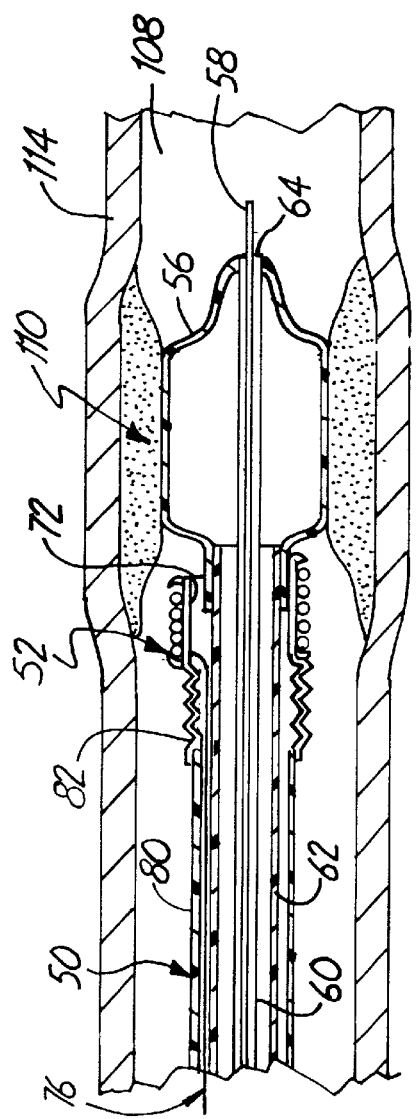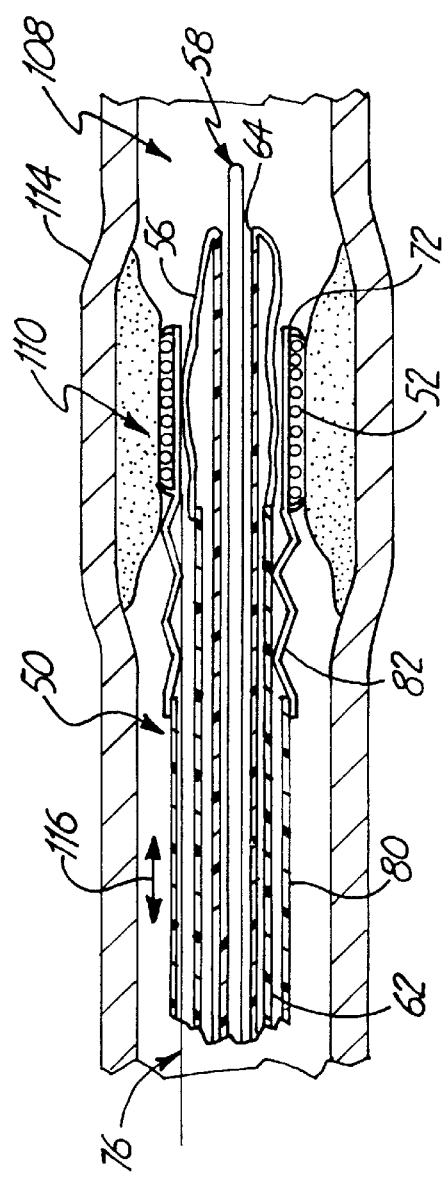

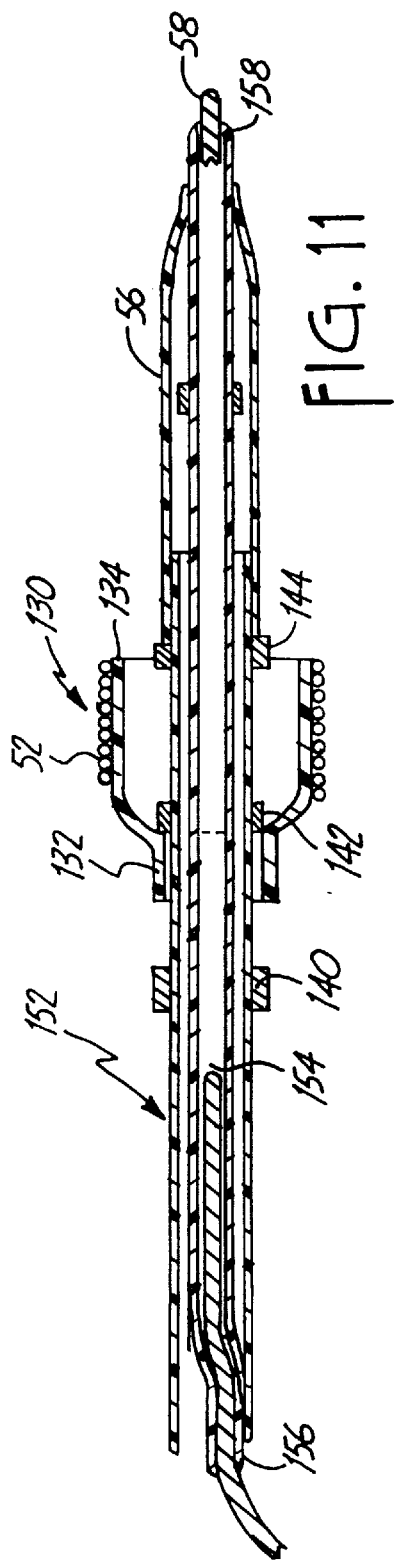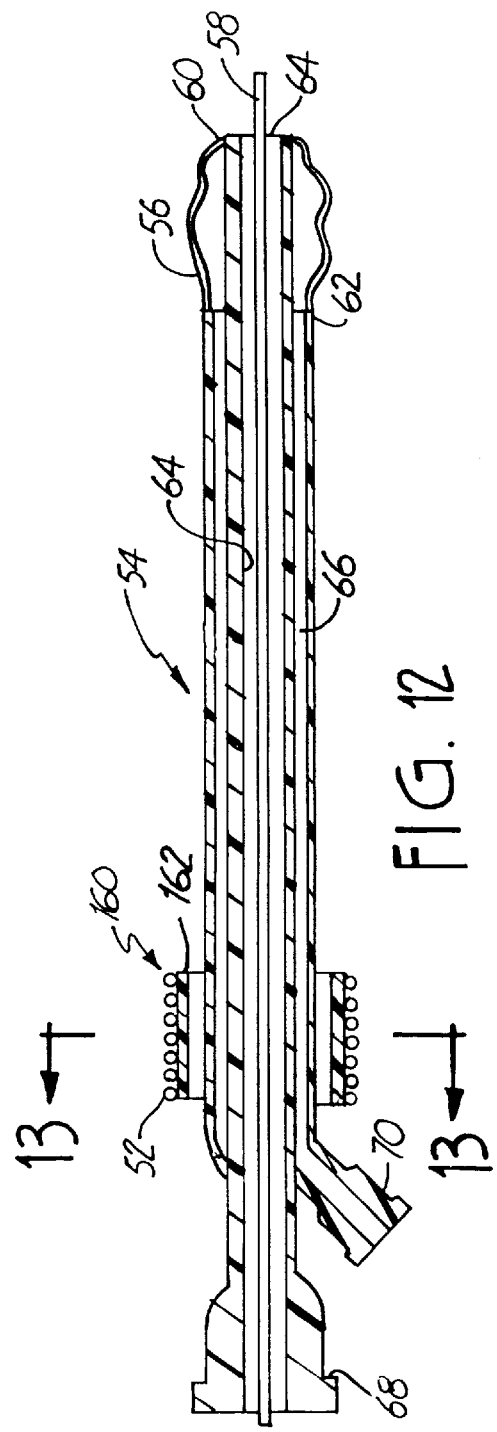

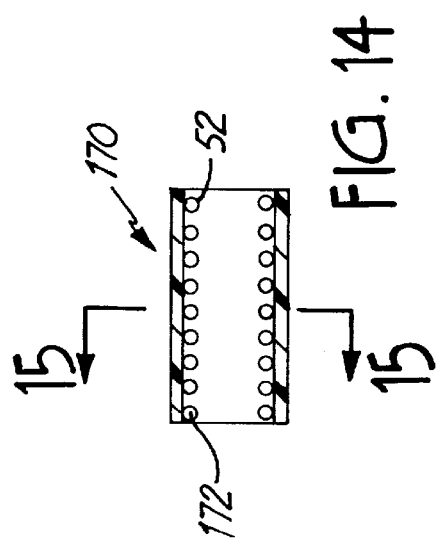
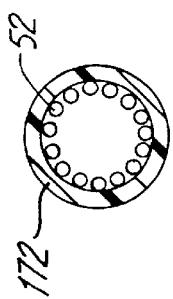
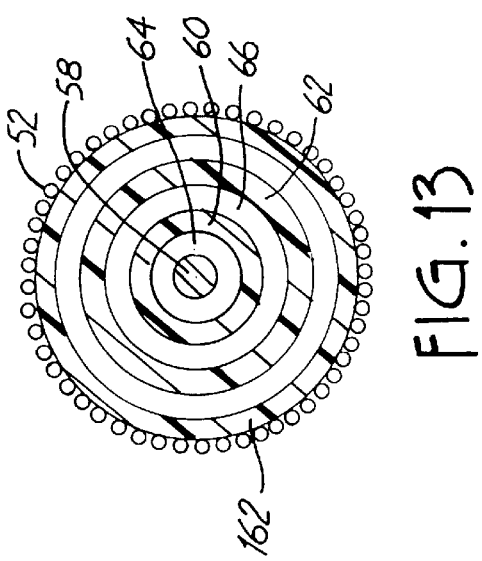

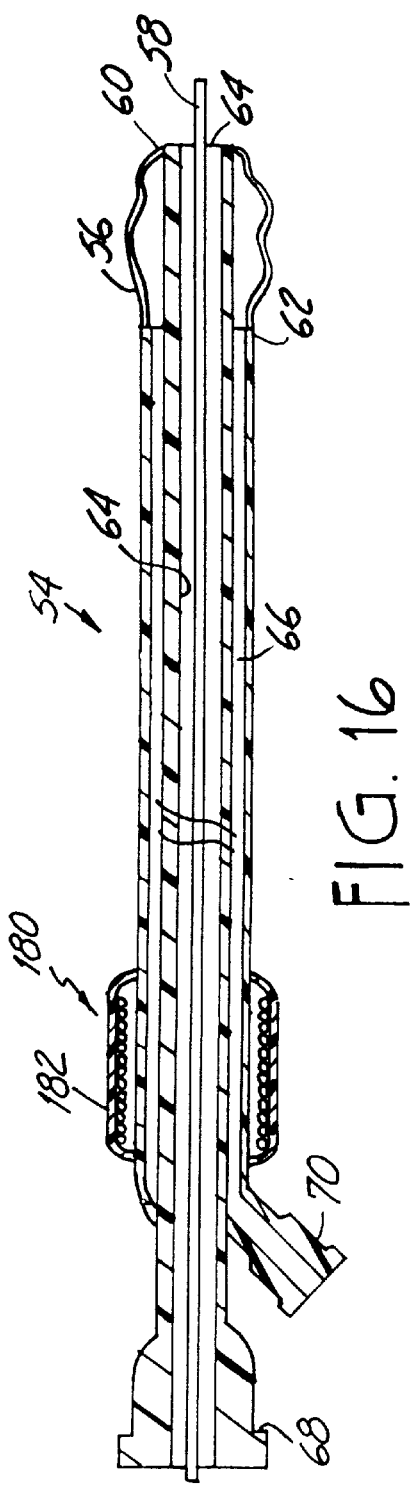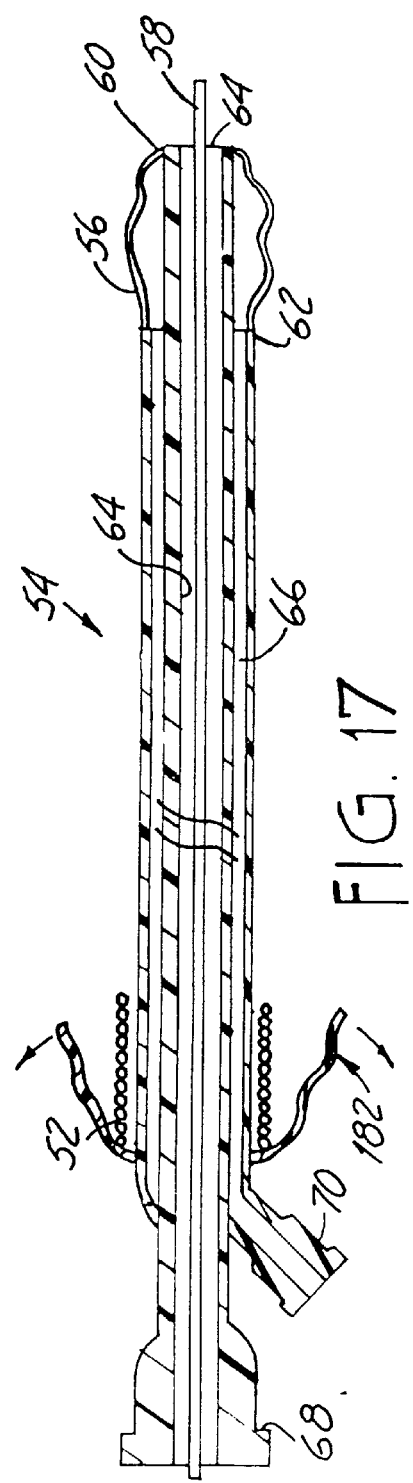

ND METHOD

BACKGROUND OF THE INVENTION

The present invention relates to a stent deployment system and apparatus. In particular, the present invention relates to an improved stent deployment system for use with a catheter for deployment.

It is well known to use balloon angioplasty catheters for dilating various vessels of human bodies and most particularly for opening stenotic or restricted coronary arteries. It is also well known to place stents into vessels to maintain patency of a dilated vessel. In such systems, a balloon angioplasty or dilatation catheter is inserted into a patient and advanced to align a dilatation balloon with a lesion. Inflation pressure is supplied to the balloon to open the lesion. Stents are inserted into a patient in a collapsed condition and are deployed to conform to the shape of a dilated vessel. Balloon expandable or self expanding stents are known.

The dimensions of coronary arteries are relatively small. Thus, it is a very difficult and arduous task to track treatment devices to a lesion site in coronary arteries. Stents may be deployed by catheter devices including an inflatable balloon at a distal end. Such catheter devices may be used to dilate a lesion in addition to stent deployment. To facilitate deployment of a stent via a catheter, it is desirable to provide a device that does not interfere with dilatation and which can be easily maneuvered to a treatment site for deployment without damage.

SUMMARY OF THE INVENTION

The present invention relates to an improved stent deployment system which may be adapted for dilating a lesion and deploying a stent to maintain the patency of a dilated vessel. The stent deployment system includes an expandable stent and a stent sheath which carries the stent. The stent sheath is movably coupled to a catheter shaft of a catheter and is insertable thereby to a lesion site for deployment. The stent sheath is movably coupled to the catheter shaft for operation between a proximally-retracted insertion position and an advanced deployment position aligned with a balloon at a distal end of the catheter. The extent of the movable stent sheath is relatively short in comparison to the catheter shaft. In the proximally-retracted insertion position, the stent sheath and stent are positioned out of alignment with the balloon. In the advanced deployment position, the stent and stent sheath are aligned with the dilatation balloon for deployment of the stent via inflation of the balloon.

BRIEF DESCRIPTION OF THE DRAWINGS

FIGS. 4A–4E illustrate operation of an embodiment of a stent deployment apparatus of the present invention.

FIG. 11 is an elongated cross-sectional view of a single operator exchange dilatation catheter and embodiment of a stent deployment apparatus of the present invention.

FIG. 12 is an elongated cross-sectional view of a dilatation catheter and alternate embodiment of a stent deployment apparatus of the present invention.

FIG. 13 is a cross-sectional view taken along line 13—13 of FIG. 12.

FIG. 14 is an elongated cross-sectional view of an alternate embodiment of a stent deployment apparatus of the present invention.

FIG. 15 is a cross-sectional view taken along line 15—15 of FIG. 14.

FIG. 16 is an elongated cross-sectional view of a dilation catheter including an alternate embodiment of a stent deployment apparatus.

FIG. 17 is an elongated cross-sectional view of the embodiment of the stent deployment apparatus of FIG. 16 illustrating the protective package or covering removed for use. It should be understood that the drawings are not to scale and are for illustration purposes only.

DETAILED DESCRIPTION OF THE PREFERRED EMBODIMENTS

Figure 1:
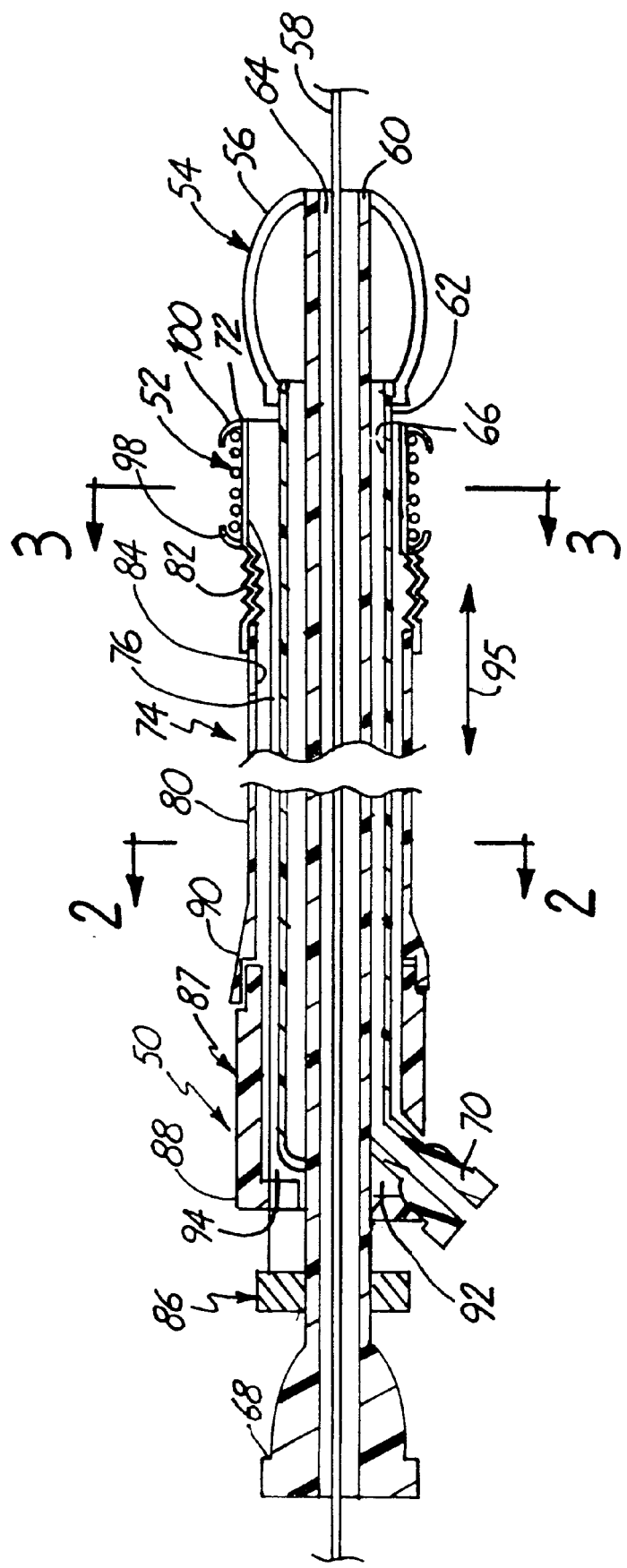
FIG. 1 is an elongated cross-sectional view of a dilatation catheter having an embodiment of a stent deployment apparatus of the present invention formed integrally therewith.
Figure 3:
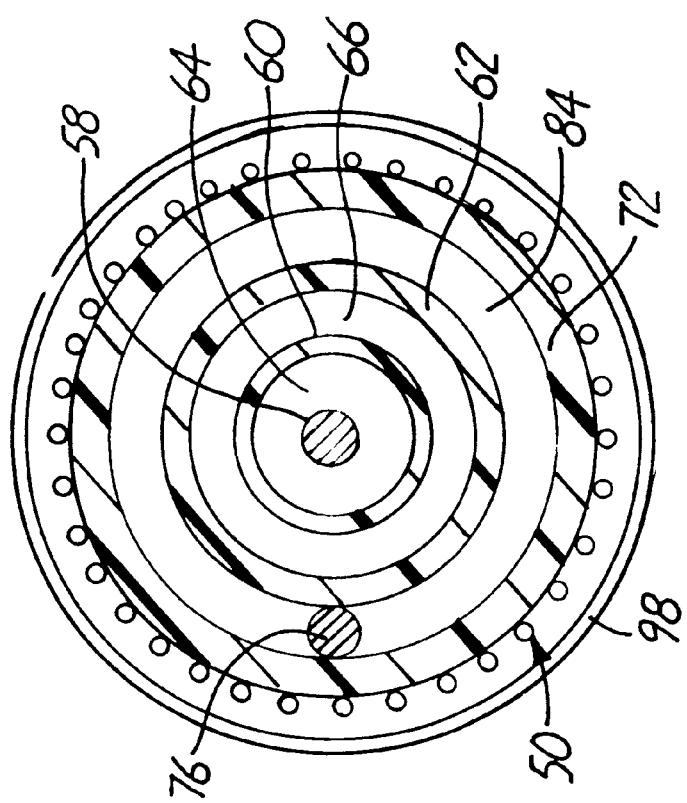
FIG. 3 is a cross-sectional view taken along line 3—3 of FIG. 1.
Figure 2:
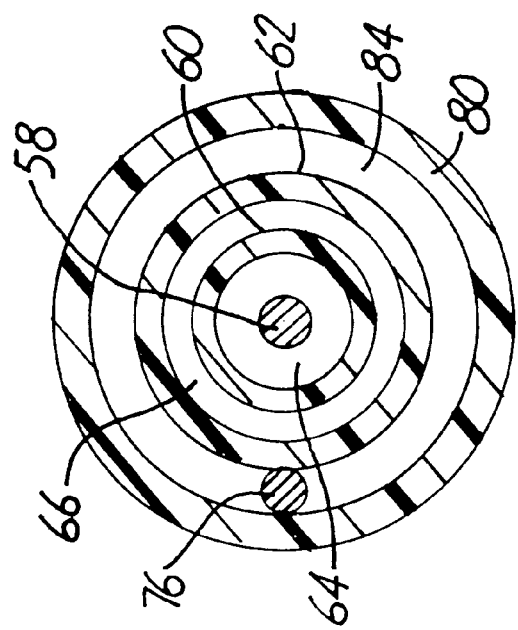
FIG. 2 is a cross-sectional view taken along line 2—2 of FIG. 1.

The present invention relates to an improved stent deployment system and apparatus. FIGS. 1–3 illustrate a first embodiment of a stent deployment apparatus 50 for deploying stent 52. As shown, the stent deployment apparatus is formed together with a dilatation catheter 54 including a dilatation balloon 56 supported at a distal end of dilatation catheter 54. As shown, the catheter is an "over-the-wire" catheter which includes a guidewire 58, an inner tube 60, and an outer tube 62. The inner tube 60 forms a guidewire lumen 64 through which guidewire 58 extends for placement of the catheter at a lesion site in a known manner. Outer tube 62 extends over inner tube 60 to define an outer shaft of the catheter. An inflation lumen 66 is formed between inner and outer tubes 60, 62.

Balloon 56 is coupled to inner tube 60 and outer tube 62 in communication with inflation lumen 66 so that introduction of fluid through inflation lumen 66 can be used for selectively inflating and deflating balloon 56. Inner tube 60 has a luer fitting 68 at a proximal end thereof, which has an inner bore in general alignment with the guidewire lumen 64. A second luer fitting 70 is coupled to the inner and outer tubes 60, 62 at the proximal end thereof to provide a fluid connection to the inflation lumen 66 for selectively supplying pressure in a known manner to inflate and deflate balloon 56.

Stent Deployment Apparatus 50

As shown, stent deployment apparatus 50 is formed integrally (such as with appropriate mechanical connections) with catheter 54 and includes stent sheath 72, support member 74, and push rod 76. The stent sheath 72 is preferably formed of a relatively short tubular member having a proximal end and a distal end. The extent between the proximal and distal ends is significantly shorter than the inner and outer tubes 60, 62 forming the catheter shaft. The stent 52 is supported about an outer surface of the stent sheath 72 and encircles the stent sheath 72 between the proximal and the distal ends. Push rcd 76 is coupled to stent sheath 72 for operating or manipulating the stent sheath 72 during deployment of stent 52, as will be explained. Support member 74 includes an elongated rigid tube portion 80 fixedly coupled to a proximal end of catheter 54 and a collapsible tube portion 82 coupled between the rigid tube portion 80 and sheath 72.

The stent sheath 72 and stent 52 are coupled to catheter 54 for insertion into a patient using support member 74. Stent sheath 72 is sized to fit over balloon 56 in the advanced deployment position. As shown, preferably, stent sheath 72 includes end caps 98, 100 on opposed ends of the stent sheath 72. The embodiment of end caps 98, 100, illustrated in FIGS. 1 and 3, is formed of a dome-shaped ring member which extends about the perimeter of stent sheath 72 at opposed proximal and distal ends to define a lip portion covering end portions of the stent 52, carried by stent sheath 72.

The collapsible tube portion 82 of support member 74 facilitates longitudinal movement of sheath 72 and stent 52 relative to the catheter shaft for selectively moving the stent 52 between a proximally-retracted position and distally-advanced deployment position. Rigid tube portion 80 and collapsible tube portion 82 extend concentrically about outer tube 62 to define a push rod channel 84 therethrough. Push rod 76 extends through channel 84 for longitudinally moving sheath 72 between the retracted position and the advanced deployment position, as illustrated by arrow 95 and as will be explained.

Preferably, as shown, push rod 76 includes an operating knob 86 at a proximal end for movement of sheath 72 between the retracted position and the advanced deployment position. Operating knob 86 is preferably formed of a ring member which extends about the proximal end of catheter 54, in particular, about inner tube 60 of catheter 54. Rigid tube portion 80 is coupled to outer tube 62 of catheter 54 via hub 87. Hub 87 includes a cup-shaped portion 88 and a tapered end member 90. The cup-shaped portion 88 includes a central opening 92 sized so that the proximal end of catheter 54 extends therethrough. Portion 88 also includes channel 94 through which push rod 76 extends. Tapered end member 90 is connected to portion 88 to provide a desired outer profile suitable for transluminal insertion into a patient.

Although stent deployment apparatus 50 is illustrated with an "over-the-wire"-type dilatation catheter system, it should be understood that the invention is not so limited and that alternate catheter designs may be used, such as a "fixed-wire" catheter or a "single operator exchange catheter." For a "single operator exchange catheter," support member 74 includes a distal opening through which guide wire 58 extends for alignment exterior to the device. Additionally, the apparatus 50 is not limited to the particular construction shown, and other constructions may be employed. For example, the collapsible tube portion 82 may be fixed to hub 87, and rigid tube portion 80 may be fixed to sheath 72. Additionally, although stent sheath 72 is shown with end caps 98 in a preferred embodiment, end caps 98 may be omitted.

Operation Of Apparatus 50

FIGS. 4A–4E illustrate operation of the stent deployment apparatus 50 and dilatation catheter 54. As shown, catheter 54 is inserted into obstructed vessel 108 to dilate lesion 110. Catheter 54 is inserted until the dilatation balloon 56 is aligned with lesion 110. The length of the support tube 74 (i.e. rigid tube portion 80 and collapsible tube portion 82) locates the stent 52 and stent sheath 72 proximate to balloon 56 in the retracted position. As previously explained, in the embodiment shown, stent deployment apparatus 50 is integrally formed with catheter 54. Stent 52 and stent sheath 72 are positioned out of axial alignment with balloon 56 in a proximally-retracted position for insertion and initial dilatation.

As shown in FIG. 4B, once the dilatation balloon 56 is aligned relative to lesion 110, the balloon 56 is inflated by supplying fluid pressure through luer fitting 70 and inflation lumen 66. Since the stent and stent sheath 72 are out of alignment with balloon 56 in the retracted position, the pressurized balloon 56 supplies pressure to the lesion 110, which compresses into the vessel wall 114 and expands the vessel wall 114 to open the constriction caused by the lesion 110. This process may be repeated in order to sufficiently compress lesion 110 into the vessel wall 114 and expand the vessel wall 114 to reduce obstruction in vessel 108.

Stent 52 is then deployed to hold the obstructed vessel 108 in an opened, nonoccluded condition. After dilatation is complete, balloon 56 is deflated, and stent 52 and stent sheath 72 are advanced over deflated balloon 56 until they are aligned with the dilatation balloon 56 for deployment, as illustrated in FIG. 4C. The stent sheath 72 and stent 52 are advanced by operation of push rod 76 which is advanced as illustrated by arrow 116 in FIG. 4C. Force is supplied by manipulation of rod 76, to a proximal end of the stent sheath 72 to advance the stent sheath 72 to the deployment position in alignment with the dilatation balloon 56.

Figure 4A:
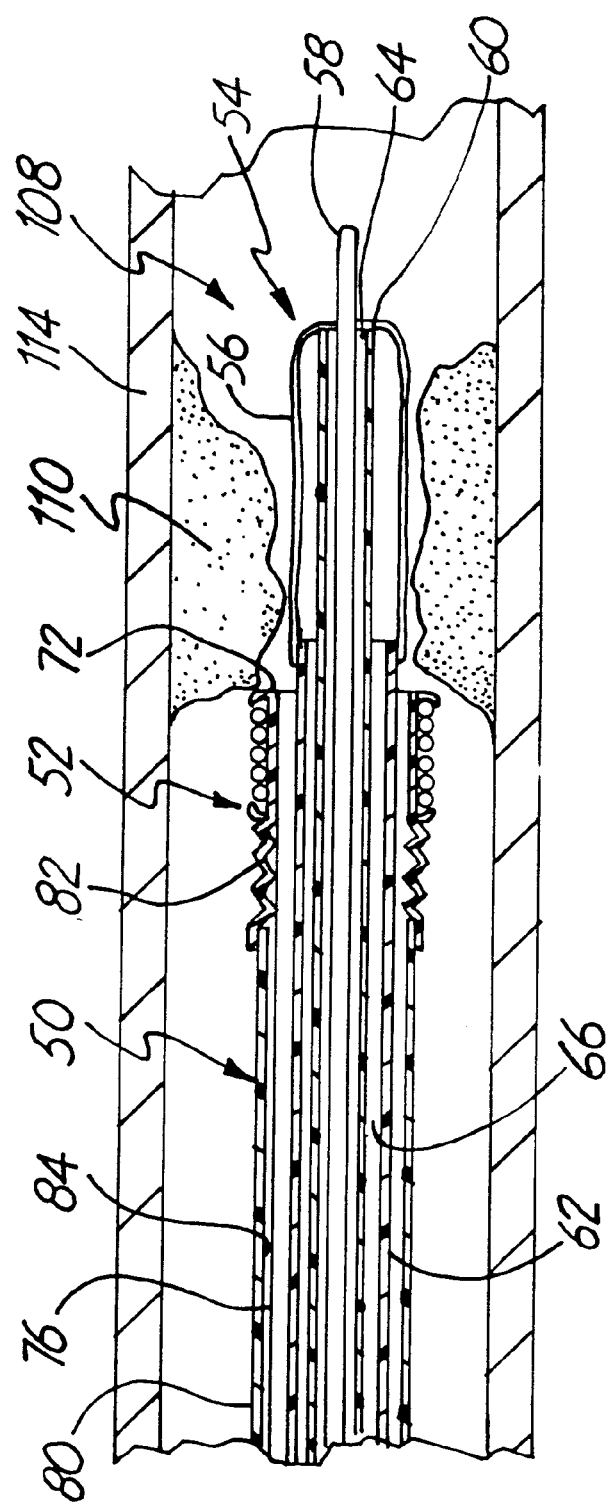
Figure 4D:
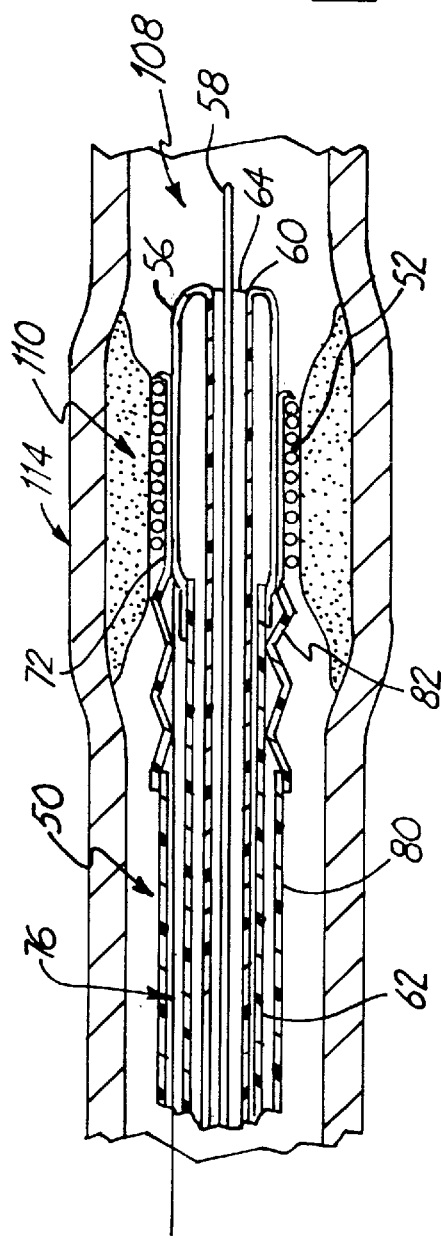

As previously explained, the stent sheath 72 is movably coupled to catheter 54 via collapsible tube portion 82, which selectively expands and contracts to accommodate movement of sheath 72 between the retracted position out of alignment with balloon 56 as shown in FIGS. 4A-4B and the advanced deployment position aligned with balloon 56 as shown in FIGS. 4C-4D. Once stent 52 and stent sheath 72 are properly aligned, as illustrated in FIG. 4D, balloon 56 is again inflated to deploy stent 52.

Figure 4E:
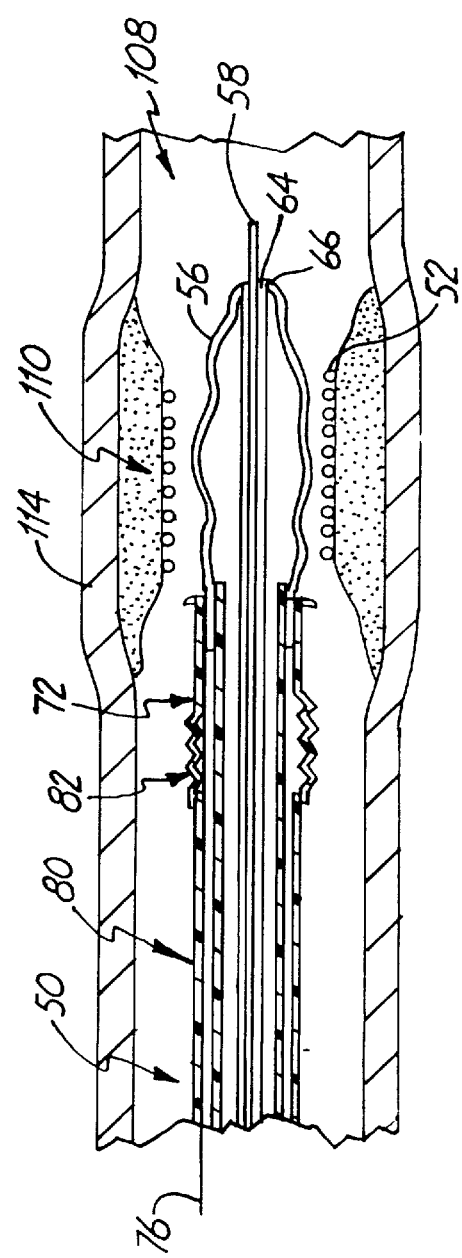

Preferably, the stent sheath 72 is formed of an elastomeric material which expands upon radial pressure introduced to the stent sheath via the balloon 56. The collapsible tube portion 82 also allows for expansion of the stent sheath 72 relative to rigid tube portion 80. Stent sheath 72 is expanded from an insertion diameter (sized for insertion through a patient's vasculature) to a deployment diameter to force stent 52 into engagement with vessel wall 114 at lesion 110 for deployment. Inflation pressure is released to deflate balloon 56 when the stent 52 is secured to vessel wall 114. The stent sheath 72 is formed of a sufficiently elastic material so that once inflation pressure is released, the stent sheath 72 has sufficient elasticity to "snap" back, or return, to a lower profile, and preferably to its preexpanded profile. Thus, sheath 72 easily separates from stent 52, which remains in place to support vessel wall 114 in an open, nonoccluded, substantially unrestricted position as shown in FIG. 4E. Although an elastomeric stent sheath 72 is shown, alternate embodiments of an expandable stent sheath 72 may be employed.

As can be seen, sheath 72 is preferably formed to perform a number of functions. Stent sheath 72 is preferably formed to provide a protective barrier between the balloon 56 and the stent 52 so that placement of the stent 52 over balloon 56 for deployment does not puncture or rip balloon 56. Further, sheath 72 is formed to protect balloon 56 from damage by the stent 52 when the balloon 56 is inflated for deployment. Sheath 72 also preferably provides means for separating the compliant balloon 56 from the stent 52 for removal after deployment of stent 52, as well as applies force to facilitate rewrapping of balloon 56 for withdrawal of the device 50. Since stent sheath 72 facilitates separation, this further limits or reduces the likelihood of damage to the balloon 56 during separation from stent 52.

As shown in FIG. 4E, once stent 52 is deployed and the inflation pressure is released from the stent sheath 72, the catheter 54 is withdrawn or repositioned for subsequent operation. Prior to moving catheter 54, the stent sheath 72 may be retracted by proximally retracting push rod 76 using knob 86 (not shown in FIGS. 4A–4E). Preferably, the stent sheath 72 is formed of a polymer material such as polyethylene, polypropylene, urethane, techtothane, or SURLYN with a stainless steel coil reinforcement braid. End caps 98, 100 are preferably formed of a urethane or polyethylene material. Push rod 76 is preferably formed of a stainless steel material, and operating knob 86, coupled to push rod 76, is preferably formed of a polycarbonate material. Hub 87 is preferably formed of a polycarbonate material.

Collapsible tube portion 82 is preferably manufactured by winding a wire or other suitable coil around a collapsible material such as a tube of SURLYN. The coil winder controls the pitch or distance between adjacent wraps of wire. After the wire is wound around the tube, the tube is pressurized, causing the tube material to expand between the gaps in the wire, creating the pleats or creases which allow portion 82 to collapse. The coil is then removed, leaving the collapsible portion 82. Construction of the collapsible portion 82 is described in St. Germain, U.S. Pat. No. 5,534,007, issued Jul. 9, 1997, and assigned to Scimed Life Systems, Inc., which is hereby incorporated by reference.

Rigid tube 80 is preferably formed of a polyester or polyether ether keytone (PEEK) material. Collapsible tube potion 82 is secured to rigid tube portion 80 and sheath 72 by a suitable adhesive as is known in the art. Alternatively, the rigid tube portion 80, collapsible tube portion 82 and sheath 72 may be integrally formed as a single unitary member. Although a preferred construction is described, it should be understood that the invention is not so limited.

Other Embodiments

Figure 6:
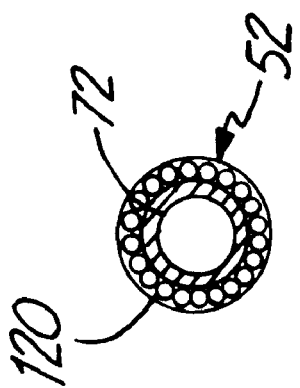
FIG. 6 is a cross-sectional view taken along line 6—6 of FIG. 5.
Figure 5:
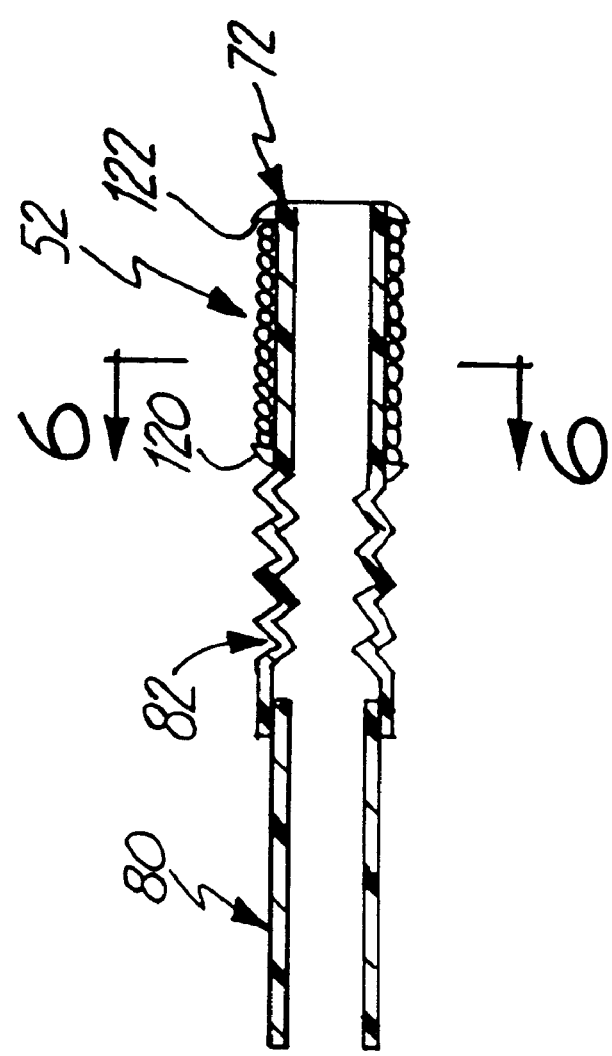
FIG. 5 is an elongated cross-sectional view of a distal portion of an alternate embodiment of the stent deployment apparatus of the present invention.

End caps 98, 100 provide a protective cover for advancing stent 52 through obstructed vessel 108 of a patient. End caps 98, 100 provide a barrier between stent 52 and vessel walls 114 to facilitate insertion of stent 52 into a patient for deployment. FIGS. 5–6 illustrate an alternate embodiment of end caps 120, 122 for providing a barrier between stent 52 and vessel walls 114 and dilatation balloon 56. As shown in FIGS. 5–6, the end caps 120, 122 are formed of an extended ridge which is formed about the perimeter of proximal and distal ends of the stent sheath 72. Caps 120, 122 are preferably tapered from an inner diameter approximately the same as the outer diameter of sheath 72 to an outer diameter roughly the same as, or just larger than, the outer diameter of stent 52.

Figure 7:
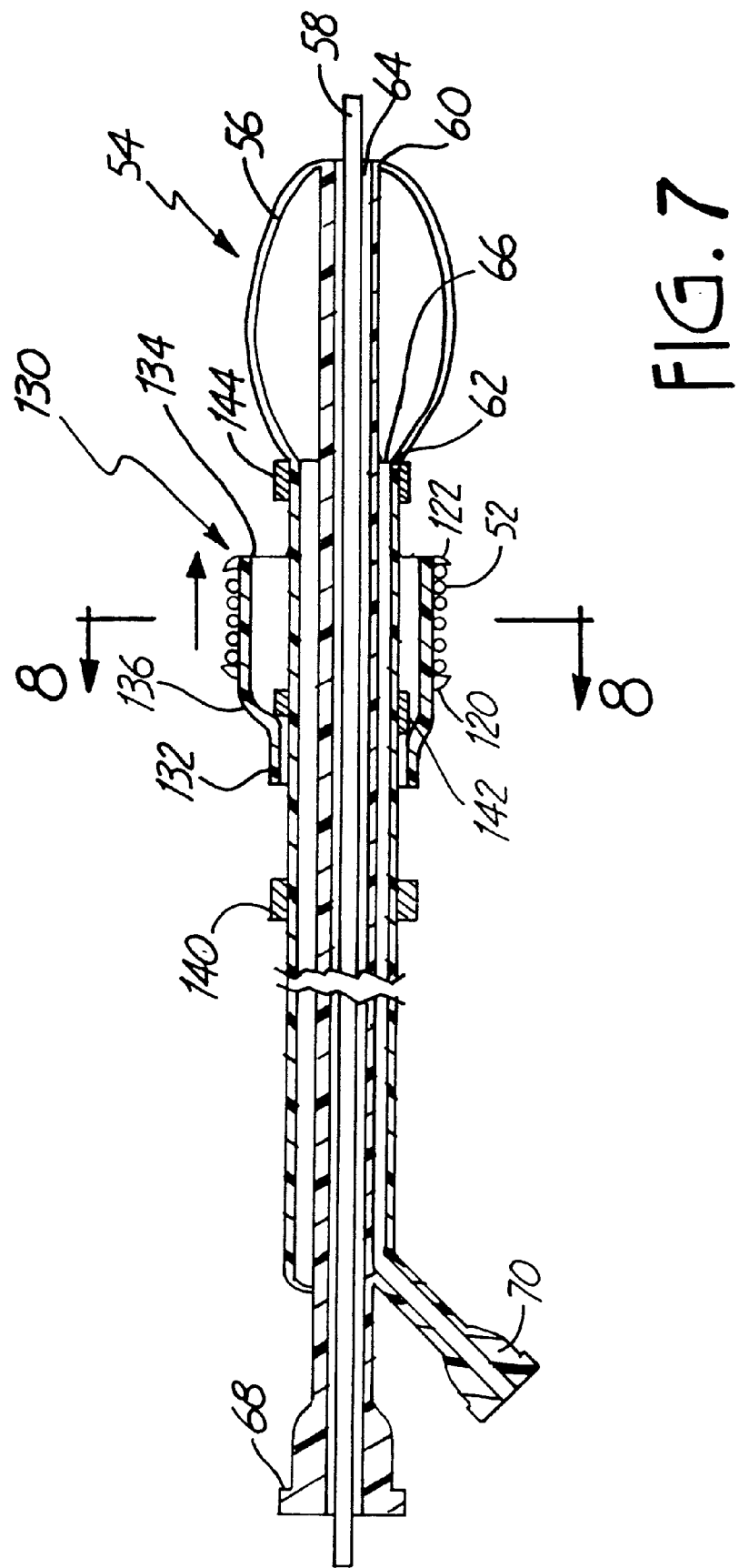
FIG. 7 is an elongated cross-sectional view of a dilatation catheter including an alternate embodiment of a stent deployment apparatus of the present invention.
Figure 8:
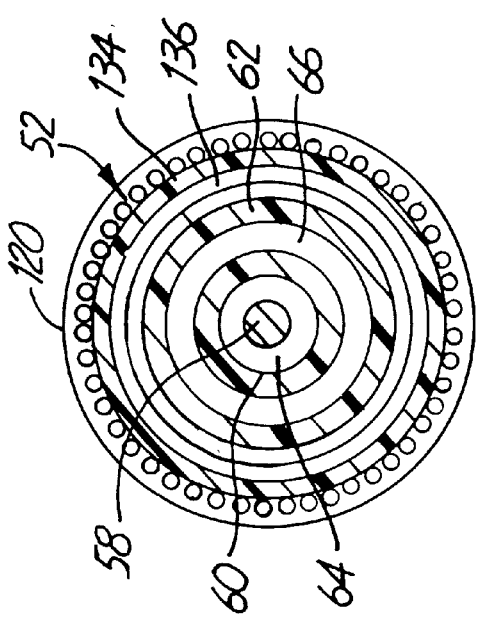
FIG. 8 is a cross-sectional view taken along line 8—8 of FIG. 7.

FIGS. 7–8 illustrate an alternate embodiment of a stent deployment apparatus 130. As shown, the stent deployment apparatus 130 is coupled to an "overthe-wire" catheter 54 similar to that illustrated in FIGS. 1–3, in which like numbers are used to refer to like parts. It should be understood that the stent deployment apparatus 130 illustrated in FIG. 7 may be incorporated with alternate-type catheter systems such as a fixed-wire catheter or a "single operator exchange" catheter, as will be explained. As shown, the stent deployment apparatus 130 includes support member 132, stent sheath 134.

Support member 132 is a shortened tube having a diameter sized for slidable placement over outer tube (or catheter shaft) 62 and is slidable therealong. Sheath 134 is coupled to (e.g. either mechanically attached to, or integrally formed with) support member 132 and has an open distal end with an inner diameter sized to slide over and receive deflated balloon 56. Sheath 134 also has an outer surface configured to carry stent 52. Support member 132 and sheath 134 form a relatively short, funnel-shaped member in comparison to the catheter shaft, which is movable relative to the catheter shaft. The funnel-shaped member has a tapered transition portion 136 which connects sheath 134 and support member 132. Preferably, the funnel-shaped member is formed of a unitary construction by known manufacturing techniques. The transition portion 136 provides a flexible connection between stent sheath 134 and the support tube 132 to allow for expansion of the stent sheath 134 relative to support tube 132 to deploy stent 52.

As shown in FIG. 7, the stent sheath 134 is in a proximally-retracted position (out of alignment with the balloon 56 but preferably proximate to the balloon 56 for easy alignment with the balloon 56) for insertion of the catheter into the vasculature. The catheter is then used to dilate a lesion via inflation of dilatation balloon 56 as previously explained in FIGS. 4A–4E. Movement of the stent deployment system 130 (or support tube 132) is controlled using rings 140, 142, 144. Stop ring 140 is formed of a relatively rigid material and has an inner diameter sized to fit over outer tube (or catheter shaft) 62 of catheter 54. The stop ring 140 is placed to provide a back stop for restricting proximal movement of the stent deployment apparatus 130. In particular, stop ring 140 is aligned relative to a proximal end of the support tube 132 to provide a backstop for locking the stent deployment apparatus 130 at the distal end of the catheter 54 proximate to the balloon 56 for insertion and use.

Rings 142, 144 restrict distal movement of the stent deployment apparatus (and sheath 134) and are sized to fit over outer tube (or catheter shaft) 62. Stop ring 142 is aligned relative to movable support tube 132 to define a retracted position for the stent deployment apparatus 130, where sheath 134 is out of alignment with balloon 56 or preferably proximal to the balloon 56 so that the balloon may be inflated to dilate a lesion. Stop ring 142 prevents independent distal movement of the stent deployment apparatus 130 so that the stent deployment apparatus 130 does not interfere with inflation of the balloon 56 during dilatation of lesion 110.

Preferably, for coronary vessel procedures, stop ring 142 is aligned so that the stent deployment apparatus 130 remains in the guide catheter (not shown) while the balloon 56 dilates a lesion in the arteries. Although stop ring 142 can be positioned to locate stent deployment apparatus 130 out of alignment with balloon 56 and not necessarily the guide catheter (not shown). Movement of stent deployment apparatus 130 may be facilitated by hand or alternatively by an elongated push rod (not shown) coupled to the deployment apparatus 130 and having sufficient length outside the patient for placement of the deployment apparatus 130 (and stent 52) relative to a treatment site.

In the embodiment shown in FIG. 7, the position of the stent deployment apparatus 130 may be adjusted by handsliding the device 130 along the catheter shaft 62. If the position of the deployment apparatus 130 is adjusted after dilatation, then catheter 54 is first withdrawn from the patient prior to moving the stent deployment apparatus 130 to align with balloon 56. The dilatation catheter 54 is withdrawn from the patient along guidewire 58. Stent sheath 134 is then positioned relative to balloon 56 and the catheter 154 such that the stent sheath 134 is positioned over the balloon 56. The stent sheath 134 may be crimped down (by hand or by a crimping tool not shown) relative to the catheter shaft to secure the stent sheath 134 for insertion.

Catheter 54 and stent sheath 134 are then reinserted and advanced along guidewire 58 to the lesion site to deploy stent 52. Pressure is supplied to the stent sheath 134 via balloon 56 to expand sheath 134 to the deployment diameter to deploy stent 52. After the stent 52 is deployed, pressure is released so that sheath 134 collapses or snaps back as previously explained to the insertion diameter (or at least to a diameter smaller than the deployment diameter). Alternatively, sheath 134 can be formed of material which collapses sufficiently that it frictionally engages balloon 56 even if balloon 56 is completely collapsed.

Preferably, stop ring 142 is formed of a relatively compressible material with sufficient rigidity to lock member 132 against movement unless forcibly moved. Stop ring 142 is sufficiently compressible so that when an actuation force is applied to the support member 132, stop ring 142 compresses so that the support member 132 may be advanced over stop ring 142 for movement of the stent deployment apparatus 130 to the advanced deployment position. Alternatively, the member 132 may be sufficiently flexible to move past stop ring 142 via an actuation force.

Stop ring 144 is aligned relative to dilatation balloon 56 to define an advanced deployment position. The stop ring 144 is formed of a relatively rigid material so that it restricts movement of the stent sheath 134 so that the stent sheath 134 is properly aligned across the lesion 110 and balloon 56 for proper placement of the stent 52. In the advanced deployment position, stent 52 and sheath 134 are aligned over balloon 56 for deployment upon inflation of balloon 56 as previously illustrated in relation to FIGS. 4C–4D. Stop ring 144 also serves as a mechanism to restrict stent sheath 134 from being pushed off the distal end of catheter 54.

The stent sheath 134 of stent deployment apparatus 130 is designed similar to stent sheath 72 of FIG. 1. Thus, sheath 134 is preferably formed of a relatively elastic material which expands upon inflation of dilatation balloon 56 to a deployment diameter and which "snaps" back into place to separate stent 52 from sheath 134 when balloon 56 is deflated. The shortened support tube 132 reduces the contact surface area between tube 132 and tube 62, thus reducing friction during slidable placement of the stent sheath 134 relative to the dilatation balloon 56. Further, the reduced length of tube 132 facilitates insertion to the treatment site and enhances maneuverability of the catheter 54 and stent deployment apparatus 130 through the patient's vasculature.

Figure 9:
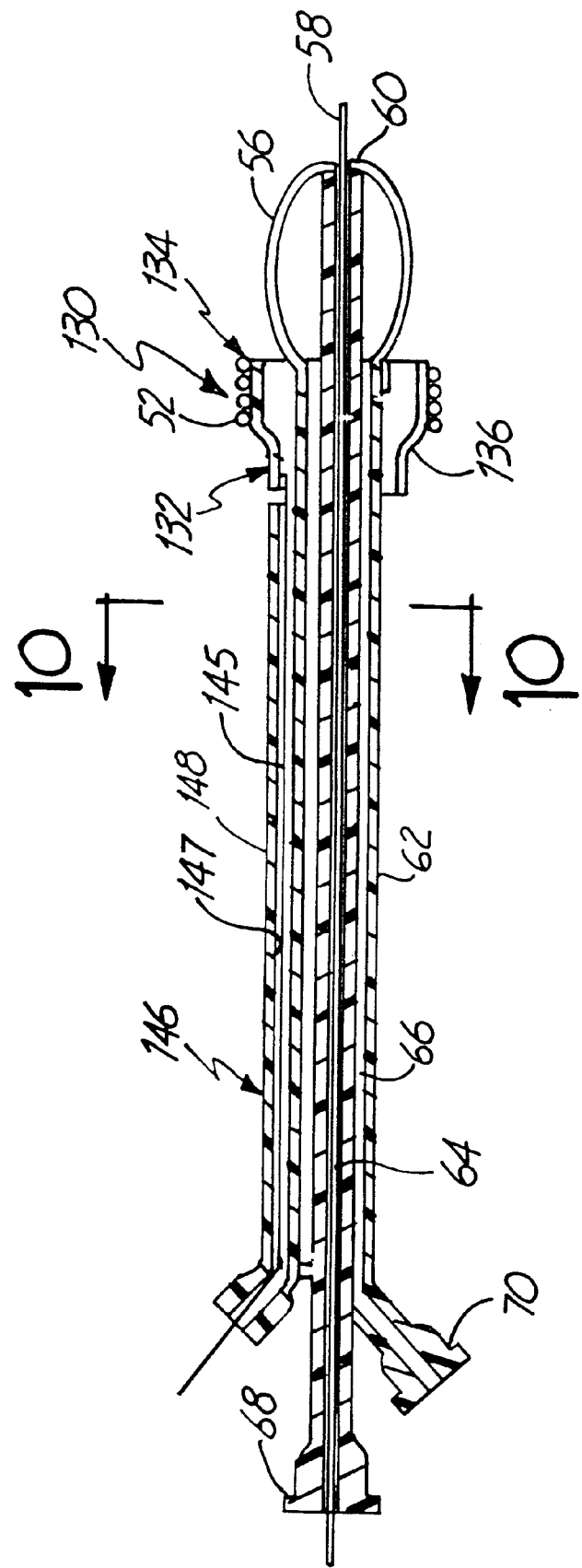
FIG. 9 is an elongated cross-sectional view of an alternate embodiment of a dilatation catheter and stent deployment apparatus of the present invention.
Figure 10:
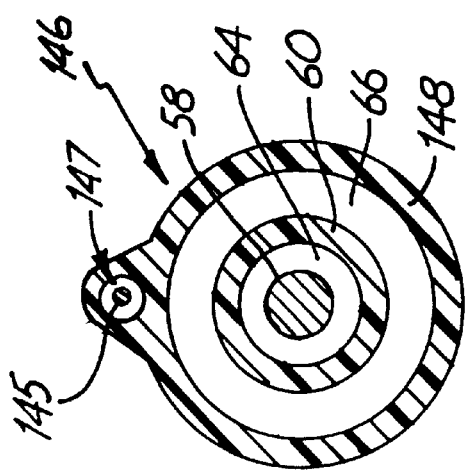
FIG. 10 is a cross-sectional view taken along line 10—10 of FIG. 9.

Alternatively, as shown in FIGS. 9–10, the stent deployment apparatus 130 may include a push rod 145 coupled to or used with an alternate catheter 146 which includes a push rod lumen 147 which extends along the length of the catheter. Catheter 146 is formed similar to catheter 54, and like numbers are used to identify like parts. Outer tube 148 of catheter 146 extends about inner tube 60 to define an outer catheter shaft. The shaft includes a first lumen which is concentrically aligned with inner tube 60 to form inflation lumen 66 and a second lumen spaced from the first lumen which is aligned to define the push rod lumen 147 therethrough. Push rod 145 extends through push rod lumen 147, as illustrated in FIGS. 9–10.

As previously explained, the stent deployment apparatus of the present invention may be employed with "over-the-wire" dilatation catheters; "fixed-wire" dilatation catheters; or, alternatively, a single operator exchange catheter 152, as illustrated in FIG. 11. Like numbers are used to refer to like parts of catheters illustrated in FIGS. 1–10. As shown, the single operator exchange catheter 152 includes a distal guidewire lumen 154 which includes proximal and distal ends 156, 158. The extent between the proximal and distal ends 156, 158 is sized to extend only along a distal portion of the catheter as is known. As shown, stent deployment support member 132 is positioned over the catheter shaft for deployment via alignment with balloon 56. The length of member 132 is designed relative to the length of the guidewire lumen 154 so that member 132 does not interfere with the exit of guidewire 158 from proximal end 156.

FIGS. 12–13 illustrate an alternate embodiment of a stent deployment apparatus 160 used in cooperation with an "over-the-wire" catheter where like numbers are used to refer to like parts shown in FIGS. 1–11. Stent deployment apparatus 160 includes a stent sheath 162 for supporting stent 52 and is a relatively short tubular member in comparison to the catheter shaft. Stent sheath 162 is formed similarly to stent sheath 72 which supports stent 52 about an outer surface thereof. The stent sheath 162 is supported prior to use at a proximal end of the catheter shaft to define a retracted position for the stent deployment apparatus 160. The stent sheath 162, itself, defines the support member of the deployment apparatus 160. While not in use, stent sheath 162 may be secured at the proximal end of the catheter via a clip (not shown) or via frictional engagement with the proximal manifold or a strain relief member (not shown). Preferably, stent sheath 162 is manipulated by hand.

In operation, catheter 54 is inserted in the patient, and balloon 56 is aligned relative to lesion 110. Preferably, the balloon 56 is inflated to dilate lesion 110 as previously explained in relation to FIGS. 4A–4E. Once the lesion 110 is dilated, balloon 56 is deflated and the catheter is withdrawn, and stent sheath 162 and stent 52 supported thereby are advanced by hand from the proximal end of the catheter shaft to align with the dilatation balloon 56 for deployment. The balloon 56 of catheter 54 and stent sheath 162 are advanced to the lesion 110 for deployment. Since the stent sheath 162 is preferably supported prior to use at the proximal end of the catheter shaft, the stent deployment apparatus does not interfere with the maneuverability of the catheter for dilatation.

FIGS. 14–15 illustrate another embodiment of a stent deployment apparatus 170 including a stent sheath 172. As shown in FIGS. 14–15, stent 52 is supported on an inner surface of stent sheath 172, which is formed of a biocompatible material and is deployed with stent 52 via operation of dilatation balloon 56. Stent sheath 172 is preferably supported at a proximal end of a catheter until use. Preferably, the catheter is inserted into the patient and the balloon is aligned across the lesion for dilatation. After, the lesion is dilated, the catheter is withdrawn along guidewire 58 and stent sheath 172 is crimped down on the balloon for deployment by hand or by a crimping tool (not shown). Thereafter, the catheter is inserted and advanced along guidewire 58 to align the balloon 56 (having sheath 172 and stent 52 therearound) across the dilated lesion. The balloon is inflated to deploy the stent 52 and biocompatible sheath 172 to maintain the dilated lesion in an opened, non-occluded condition.

In another embodiment of a stent deployment apparatus 180, the stent 52 is supported relative to a proximal hub (or manifold) of a dilatation catheter 54 and has a protective package or covering 182 formed therearound to protect the stent 52 prior to use. Preferably, the protective package is formed of a plastic material. Preferably, ends of the package are secured or sealed to the catheter shaft via known techniques such as heating, or are mechanically secured or sealed via clips. The stent 52 is movably supported about the catheter shaft at the proximal end and the protective package formed therearound limits movement of the stent along the catheter shaft prior to use.

For use, the dilatation catheter is inserted into a patient to align the dilatation balloon across a lesion for treatment. The balloon is inflated to dilate the lesion and the catheter is withdrawn from the patient's vasculature. Thereafter, the protective package is removed from the stent and the stent is aligned and crimped down relative to the balloon for deployment. Since, the stent is premounted on the proximal hub, the catheter does not need to be removed from the guidewire and the catheter can be reinserted along the guidewire to locate the balloon and stent relative to the lesion for deployment of the stent. The balloon is again inflated to deploy the stent.

Although the present invention has been described with reference to preferred embodiments, workers skilled in the art will recognize that changes may be made in form and detail without departing from the spirit and scope of the invention.

What is claimed is:

1. In combination:
   a catheter including an elongated catheter shaft having a proximal end and a distal end, a balloon supported at the distal end and an inflation lumen extending therethrough and in fluid communication with the balloon; and
   a stent deployment device including a tubular member having a proximal and distal end slidably coupleable along the catheter shaft and the tubular member including an expandable stent sheath expandable between a first diameter dimension and a second diameter dimension for deployment of a stent supported thereby, the length of the tubular member being sized so that the length of the balloon is at least approximately as long as the stent sheath and a length of the tubular member between the proximal end and distal end does not extend along a substantial length of the catheter shaft, the proximal end of the tubular member being without circumferential connection to a support tube for operation and use.

2. The combination of claim 1 and further comprising a stent supported and carried by an outer surface of the stent sheath.

3. The combination of claim 1 wherein the stent sheath is formed of an elastic material adapted to expand to a deployment diameter upon application of deployment pressure and sufficiently elastic to collapse to approximately an insertion diameter after deployment pressure is released.

4. The combination of claim 1 wherein the catheter shaft includes a stop ring extending about an outer perimeter thereof, said stop ring being located to define a retracted position for the stent sheath, said stop ring being sized to restrict independent movement of the tubular member thereacross and allowing passage of the tubular member thereacross upon application of sufficient force to the tubular member.

5. The combination of claim 1 wherein the catheter shaft includes a stop ring extending about an outer perimeter thereof, said stop ring being located to position the stent sheath in alignment with the balloon coupled to the catheter shaft for deployment of a stent.

6. The combination of claim 1 wherein the catheter shaft includes a back stop formed of a ring extending about an outer perimeter of the catheter shaft and positioned to limit proximal movement of the tubular member.

7. The combination of claim 1 wherein the stent sheath is formed of a biocompatible material.

8. The combination of claim 1 wherein the tubular member includes a reduced diameter portion to the support the stent sheath along the catheter shaft.

9. A dual function catheter adapted for dilation of an occluded vessel and deployment of an expandable stent comprising:
   an elongated catheter shaft having a proximal end and a distal end, and an inflation lumen extending therethrough and a dilation balloon supported at the distal end of the catheter shaft;
   an expandable stent sheath, said stent sheath being movably supported relative to the catheter shaft for alignment of the stent sheath relative to the balloon and expandable thereby for deployment of a stent supported thereby; and
   a stent sheath shaft fixed to the catheter shaft and the stent sheath is coupled to the stent sheath shaft and movable relative to the catheter shaft.

10. The dual function catheter of claim 9 wherein the stent sheath shaft includes a rigid portion and a collapsible portion to movably support the stent sheath relative to the catheter shaft.

11. A catheter comprising:
   a catheter shaft having a balloon supported at a distal end;
   a stent sheath expandable for deployment of a stent; and
   the catheter shaft including a stent sheath shaft including a rigid portion and an axially collapsible portion to movably support the stent sheath coupled to the stent sheath shaft between a retracted position and an advanced position.

12. The catheter of claim 11 wherein:
   the rigid portion includes a proximal and distal end and the proximal end is fixed to a proximal end portion of the catheter shaft; and
   the collapsible portion includes a proximal end and a distal end and the proximal end of the collapsible portion is connected to the distal end of the rigid portion.

13. A method for dilating a lesion and deploying a stent comprising the steps of:
   providing an elongated catheter shaft having a proximal end and a distal end and a dilation balloon supported at the distal end;
   providing a tubular member having a proximal and distal end and including an expandable stent sheath, the tubular member being premounted on the catheter shaft;
   inserting the catheter shaft into a patient for treatment and positioning the balloon across a lesion at a treatment site with the expandable stent sheath withdrawn from the balloon and the tubular member supported entirely on a proximal end portion of the catheter shaft;
   inflating the balloon;
   deflating the balloon;
   withdrawing the catheter shaft from the patient;
   advancing the stent sheath over the balloon;

advancing the catheter shaft with the stent sheath positioned over the balloon to the treatment site; and reinflating the balloon to deploy a stent.

14. The method of claim 13 wherein the catheter shaft is withdrawn over a guide wire and the catheter shaft and stent sheath are advanced over the guide wire.

15. The method of claim 13 wherein the stent is crimped down over the balloon.

16. The method of claim 13 including the step of:

hand manipulating the stent sheath to position the stent sheath over the balloon.

17. The method of claim 13 wherein the stent sheath is advanced over the balloon by hand.

18. A catheter comprising:

a catheter shaft having a balloon supported at a distal end and an inflation lumen extending through the catheter shaft and opened to the balloon;

a stent deployment device including a tubular member having a proximal and distal end and an expandable stent sheath;

a push rod connected to the proximal end of the tubular member; and the catheter shaft including a push rod lumen and the push rod extending through the push rod lumen of the catheter shaft.

19. The catheter of claim 18 wherein the tubular member comprises:

a proximal neck portion.

20. A method for treating a patient comprising steps of:

providing an elongated catheter shaft having a proximal end and a distal end and a dilatation balloon supported at the distal end;

providing a tubular member having a proximal and distal end and an expandable stent sheath;

slidably positioning the tubular member to align with a first stop member spaced from a proximal end portion of the catheter shaft to support the expandable stent sheath spaced from the balloon in a retracted position;

inserting the catheter shaft and expandable stent sheath with the expandable stent sheath in the retracted position into a patient for treatment and advancing the catheter shaft to position the balloon across a lesion at a treatment site;

inflating the balloon while the stent sheath is in the retracted position;

deflating the balloon;

withdrawing the catheter shaft and [expandable stent] tubular member from the patient;

grasping the tubular member proximate to the first stop member and slidably advancing the tubular member to align with a second stop member distally spaced from the first stop member to support the expandable stent sheath in an advanced position with the expandable stent sheath aligned with the balloon;

advancing the catheter shaft and the tubular member aligned with the second stop member to the treatment site; and reinflating the balloon to deploy a stent.

21. A method for treating a patient comprising steps of:

providing an elongated catheter shaft having a proximal end and a distal end and a dilation balloon supported at the distal end;

providing an expandable stent sheath premounted on the catheter shaft;

inserting the catheter shaft into a patient for treatment and positioning the balloon across a lesion at a treatment site;

inflating the balloon;

deflating the balloon;

withdrawing the catheter shaft from the patient;

grasping the stent sheath and moving the stent sheath over the balloon;

advancing the catheter shaft and the stent sheath to the treatment site; and reinflating the balloon to deploy a stent.

* * * * *